(12) United States Patent
Humphreys et al.

(10) Patent No.: US 11,068,941 B2
(45) Date of Patent: Jul. 20, 2021

(54) TECHNIQUES FOR IN-STORE PRESCRIPTION NOTIFICATIONS

(71) Applicants: Dustin Wayne Humphreys, East Greenwich, RI (US); Vijay I. Kukreja, Cumberland, RI (US); Dharmendra Gudimetla, Fountain Hills, AZ (US)

(72) Inventors: Dustin Wayne Humphreys, East Greenwich, RI (US); Vijay I. Kukreja, Cumberland, RI (US); Dharmendra Gudimetla, Fountain Hills, AZ (US)

(73) Assignee: CVS Pharmacy, Inc., Woonsocket, RI (US)

( * ) Notice: Subject to any disclaimer, the term of this patent is extended or adjusted under 35 U.S.C. 154(b) by 1331 days.

(21) Appl. No.: 14/829,160

(22) Filed: Aug. 18, 2015

(65) Prior Publication Data

US 2017/0053093 A1 Feb. 23, 2017

(51) Int. Cl.
*G06Q 30/02* (2012.01)
*G16H 10/60* (2018.01)
(Continued)

(52) U.S. Cl.
CPC ..... *G06Q 30/0268* (2013.01); *G06Q 30/0258* (2013.01); *G06Q 30/0261* (2013.01); *G06Q 30/0267* (2013.01); *G06Q 30/0271* (2013.01); *G06Q 40/08* (2013.01); *G16H 10/60* (2018.01); *G16H 20/10* (2018.01); *H04W 48/16* (2013.01); *H04W 60/00* (2013.01); *H04W 76/10* (2018.02)

(58) Field of Classification Search
None
See application file for complete search history.

(56) References Cited

U.S. PATENT DOCUMENTS 6,185,541 B1 2/2001 Scroggie
6,484,146 B2 11/2002 Day et al.
(Continued)

FOREIGN PATENT DOCUMENTS

WO 2010120358 10/2010
WO 2011014292 2/2011
(Continued)

OTHER PUBLICATIONS

MacLaughlin, E.J., Raehl, C.L., Treadway, A.K. et al. Assessing Medication Adherence in the Elderly. Drugs Aging 22, 231-255 (2005). https://doi.org/10.2165/00002512-200522030-00005 (Year: 2005).*

(Continued)

*Primary Examiner* — Lena Najarian
(74) *Attorney, Agent, or Firm* — Patent Law Works LLP

(57) ABSTRACT

A mobile device and a server exchange information in response to the mobile device detecting a proximity beacon. Upon detecting the proximity beacon, the mobile device initiates a web service call to the server. A mobile device user will indicate a choice whether to opt-in upon registration. If the user has opted in, the server will retrieve additional information about the user including prescription information. The server will transmit prescription information and other marketing information to the mobile device. The server may be configured to receive additional information from the mobile device, for example, a request for a prescription to be refilled.

12 Claims, 8 Drawing Sheets

If customer has opted in and has prescriptions eligible for refill, server sends relevant information to the mobile device
701

Mobile device displays information about prescription eligible for refill and displays message asking whether the user would like to refill now 702

If the customer indicates yes, the server calls in to the pharmacy to request a refill
703

When the prescription is ready for pick-up, the mobile device receives relevant information and displays a message that the prescription is ready for pick-up
704

(51) Int. Cl.
*H04W 76/10* (2018.01)
*G16H 20/10* (2018.01)
*G06Q 40/08* (2012.01)
*H04W 48/16* (2009.01)
*H04W 60/00* (2009.01)

(56) References Cited

U.S. PATENT DOCUMENTS

| | | |
|---|---|---|
| 6,885,994 B1 | 4/2005 | Scroggie et al. |
| 6,912,507 B1 | 6/2005 | Phillips et al. |
| 7,184,972 B2 | 2/2007 | Flaherty |
| 7,233,913 B2 | 6/2007 | Scroggie et al. |
| 7,308,254 B1 | 12/2007 | Rissanen |
| 7,860,450 B2 | 12/2010 | Rissanen |
| 8,090,355 B2 | 1/2012 | Rissanen |
| 8,219,651 B2 | 7/2012 | Amjadi |
| 8,260,320 B2 | 9/2012 | Herz |
| 8,290,506 B1 | 10/2012 | Coverstone |
| 8,315,650 B2 | 11/2012 | Lau et al. |
| 8,396,485 B2 | 3/2013 | Grainger et al. |
| 8,412,590 B2 | 4/2013 | Elliott |
| 8,515,459 B2 | 8/2013 | Busch |
| 8,548,847 B2 | 10/2013 | Roberts et al. |
| 8,589,245 B2 | 11/2013 | Michaelis et al. |
| 8,593,277 B2 | 11/2013 | Nath et al. |
| 8,595,335 B2 | 11/2013 | Arnjadi |
| 8,620,733 B2 | 12/2013 | Roberts et al. |
| 8,626,581 B2 | 1/2014 | Christensen |
| 8,630,662 B2 | 1/2014 | Herz |
| 8,670,998 B2 | 3/2014 | Bertha et al. |
| 8,700,453 B2 | 4/2014 | Scroggie et al. |
| 8,712,830 B2 | 4/2014 | Barnett et al. |
| 8,923,766 B2 | 12/2014 | Rissanen |
| 10,210,311 B1 * | 2/2019 | Taneja .................. G16H 10/60 |
| 2005/0234771 A1 | 10/2005 | Register et al. |
| 2007/0143137 A1 * | 6/2007 | Ross .................. G06F 19/3456 705/2 |
| 2011/0010229 A1 | 1/2011 | Ow |
| 2011/0029359 A1 | 2/2011 | Roeding et al. |
| 2011/0082729 A1 | 4/2011 | Carvallo et al. |
| 2012/0303440 A1 | 11/2012 | Ow |
| 2013/0030915 A1 | 1/2013 | Statler et al. |
| 2013/0041837 A1 | 2/2013 | Dempski et al. |
| 2013/0304578 A1 | 11/2013 | Kannan et al. |
| 2013/0317916 A1 | 11/2013 | Gopalakrishnan et al. |
| 2014/0122207 A1 | 5/2014 | Christensen |
| 2014/0180707 A1 | 6/2014 | Kukreja et al. |
| 2014/0244370 A1 | 8/2014 | Barnett et al. |
| 2014/0279270 A1 | 9/2014 | Bertanzetti et al. |
| 2014/0337117 A1 | 11/2014 | Besecker et al. |
| 2015/0081474 A1 | 3/2015 | Kostka et al. |
| 2015/0227890 A1 | 8/2015 | Bednarek et al. |
| 2015/0242592 A1 | 8/2015 | Weiss et al. |
| 2015/0287045 A1 * | 10/2015 | Brown .................. G06F 16/22 705/14.4 |
| 2015/0294084 A1 * | 10/2015 | McCauley ............ G06F 19/328 705/2 |
| 2015/0379650 A1 * | 12/2015 | Theobald ................ G06Q 50/12 705/15 |

FOREIGN PATENT DOCUMENTS

| | | |
|---|---|---|
| WO | 2011044335 | 4/2011 |
| WO | 2012177382 | 12/2012 |
| WO | 2013/119646 | 8/2013 |
| WO | 2013116894 | 8/2013 |
| WO | 2013169910 | 11/2013 |
| WO | 2013187935 | 12/2013 |
| WO | WO2015086529 A1 | 6/2015 |

OTHER PUBLICATIONS

International Search Report dated Oct. 4, 2016 for related International Application No. PCT/US2016/047325 (12 pages).

* cited by examiner

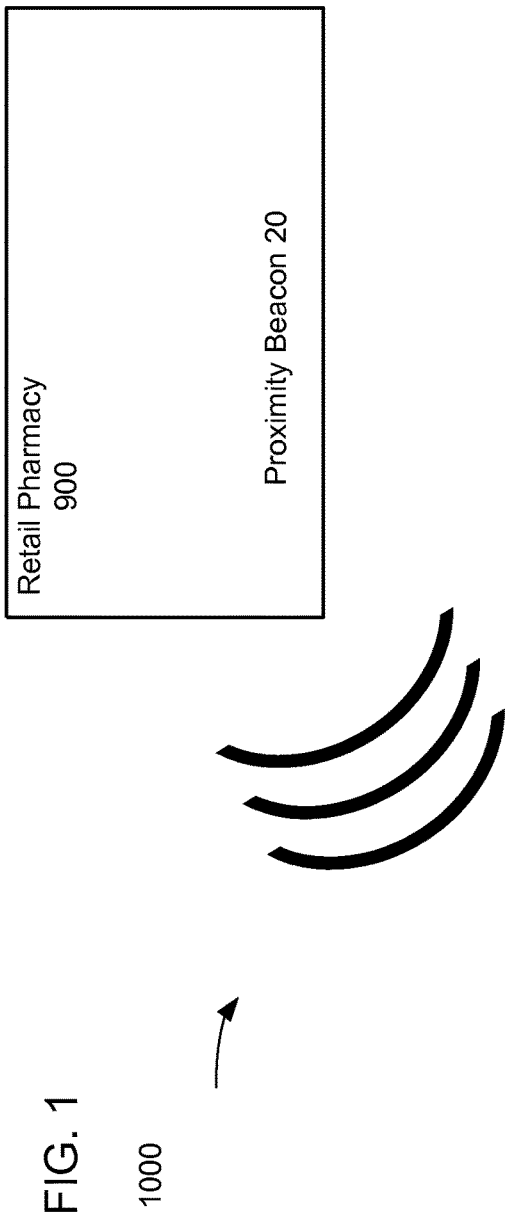
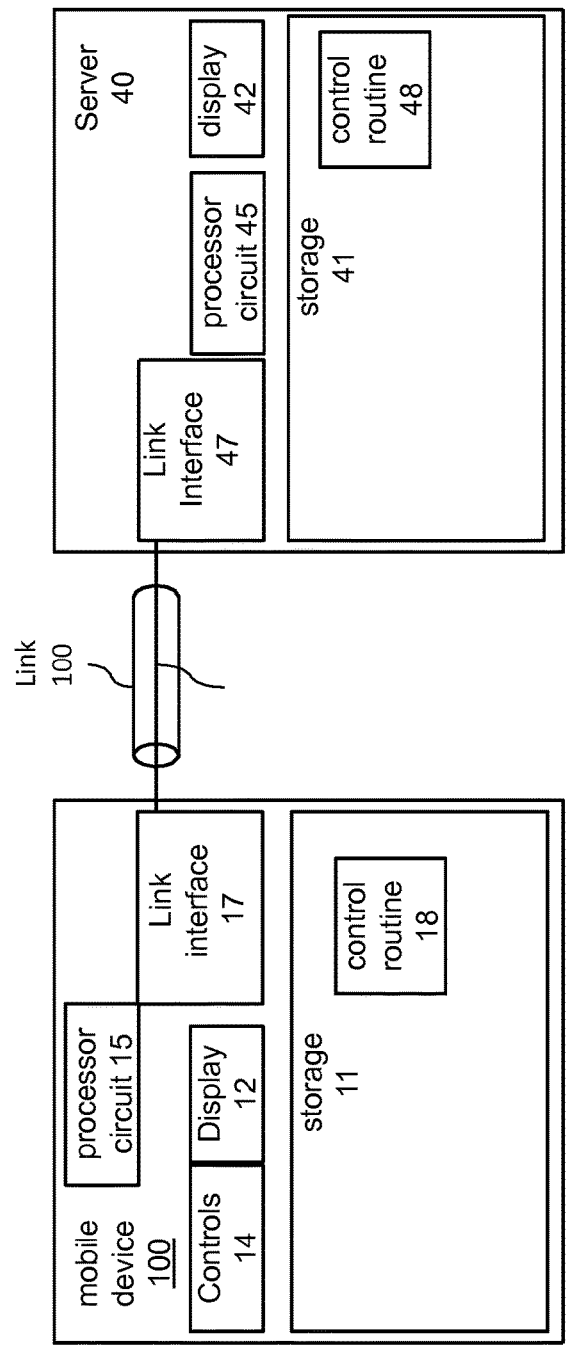
FIG. 1

If customer has opted in and has prescriptions eligible for refill, server sends relevant information to the mobile device
701

Mobile device displays information about prescription eligible for refill and displays message asking whether the user would like to refill now    702

If the customer indicates yes, the server calls in to the pharmacy to request a refill
703

When the prescription is ready for pick-up, the mobile device receives relevant information and displays a message that the prescription is ready for pick-up
704

FIG. 7

TECHNIQUES FOR IN-STORE PRESCRIPTION NOTIFICATIONS

BACKGROUND

Advances in communications technologies, including the Internet and various forms of wireless communication, have made new ways of communicating possible in a wide variety of contexts. One of those contexts relates to customer information relating to medical prescriptions. Many notification systems that provide medical prescription information are based on detecting the absolute location of a mobile device and comparing that to a predetermined set of locations of, for example, pharmacies. The comparison identifies the closest pharmacies and what the distances are. This depends on absolute location technology, such as GPS, can consume additional power, and can involve privacy issues due to identifying, and possibly storing, a mobile user's location. Additionally, the specific mobile device is often identified by a hardwired networking address called the MAC address, rather than information voluntarily and selectively entered by a user into a mobile device.

SUMMARY

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

Various embodiments are generally directed to techniques for providing in-store prescription reminders using a proximity beacon. In various embodiments, the current system provides in-store notifications to a customer's mobile device in response to the customer's mobile device detecting an in-store proximity beacon. In one aspect of the invention, the proximity-beacon system exchanges information with the mobile device including retrieving the identity of a registered user and the identity of the particular store where the proximity beacon is located. In some embodiments, this identity information is used by a server to retrieve a user's prescription records and other relevant information. This information may be provided by the server to the mobile device. The mobile device may be caused to display the retrieved information, for example, that one or more prescriptions is ready for pickup at that pharmacy. In other embodiments, the mobile device can be caused to display messages about prescriptions that are ready to be refilled and to ask the mobile device user whether to process those. That information can be provided to the pharmacy so that a refill may processed upon request.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

BRIEF DESCRIPTION OF THE DRAWINGS

FIG. 1 is a block diagram of an embodiment of an in-store prescription notification system 1000.

FIG. 7 is a flow of another embodiment of an in-store prescription notification system 1000.

DETAILED DESCRIPTION

Figure 2:
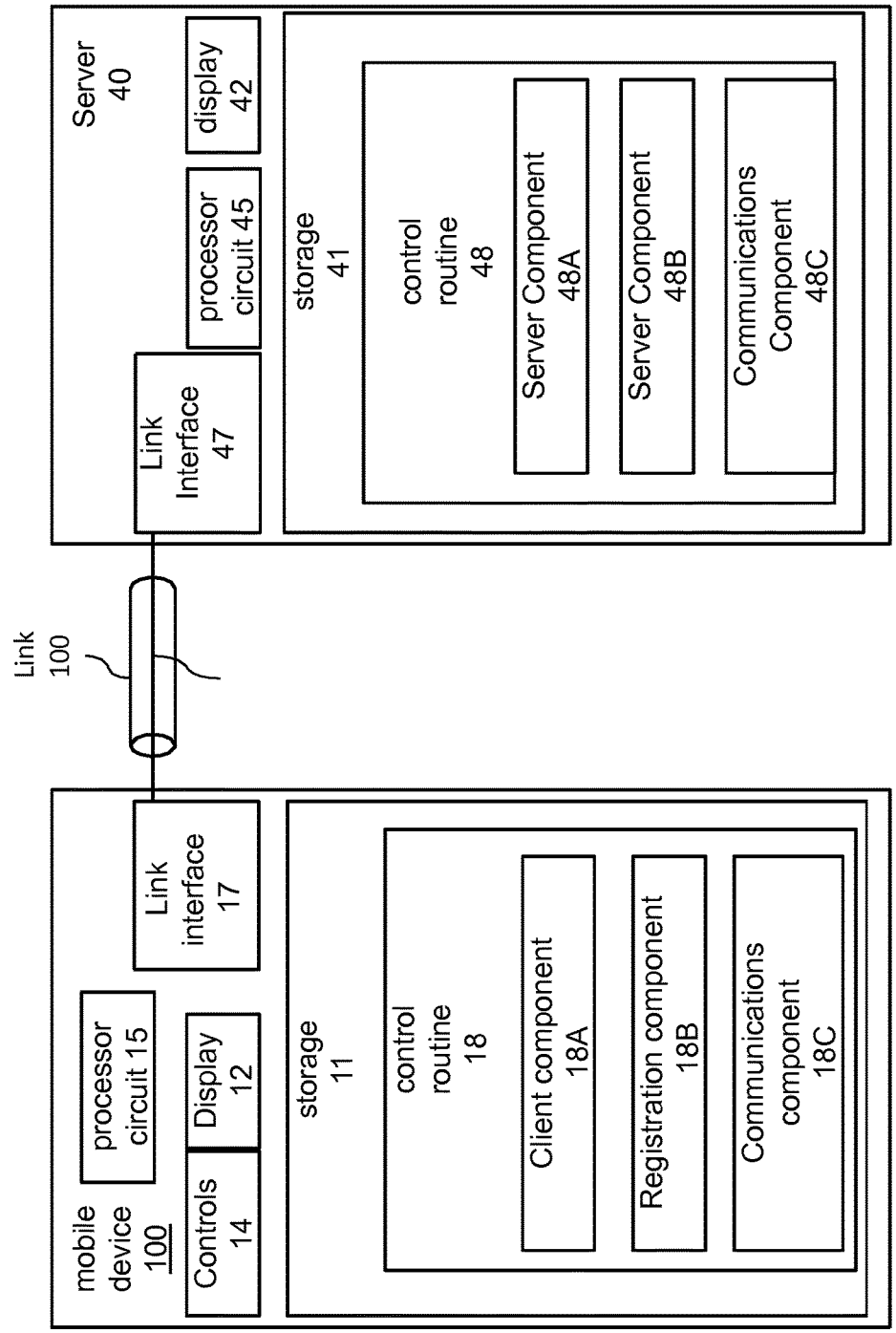
FIG. 2 is a block diagram of a portion of FIG. 1 in more detail.

Various embodiments are directed to techniques for providing in-store prescription notifications to a customer's mobile device by using proximity beam detection. A server can retrieve information relating to a registered user and send it back to the customer's mobile device. The mobile device may cause messages to be displayed, for example, that certain prescriptions are ready to be picked up. Additionally, messages can be displayed reminding a registered user that prescriptions are eligible to be refilled and asking whether the user would like to have those refilled. As a result, the embodiments can improve efficiency, modularity, power usage, and privacy, for users and stores.

With general reference to notations and nomenclature used herein, the detailed descriptions which follow may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives consistent with the claimed subject matter.

FIG. 1 is a block diagram for an in-store prescription notification system 1000 comprising one or more of a mobile device 10, a proximity beacon 20 located at a retail pharmacy 900, and a server 40. Each computing device 10 and 40 may be any of a variety of types of computing device, including without limitation, a desktop computer system, a data entry terminal, a laptop computer, a netbook computer, a tablet computer, a handheld personal data assistant, a smartphone, a body-worn computing device incorporated into clothing, a computing device integrated into a vehicle (e.g., a car, a bicycle, etc.), a server, a cluster of servers, a server farm, etc. The proximity beacon 20 is a relatively short-range wireless device that transmits a signal. In certain embodiments, the proximity range of the proximity beacon is on the order of 100-200 feet, although the subject matter is not limited in this regard. In another aspect of the invention, the mobile device 10 initiates a link 100 with the server 40 upon detecting the signal transmitted by the proximity beacon. The mobile device 10 and the server 40 may then use the link 100 to exchange information relating to the customer's identity and prescription records.

In various embodiments, the mobile device 10 comprises a storage 11 storing a control routine 18, a processor circuit 15, controls 14, a display 12, and a link interface 17 for various uses of the mobile device 10 including, without limitation, running application programs and communicating with various networks and devices such as the Internet and proximity beacon 20. It is envisioned that the mobile device 10 is likely to be a relatively portable computing device able to be carried on the person of its operator (e.g., a smartphone, a personal data assistant (PDA), a tablet computer, a watch or wearable computer, etc.). It is therefore further envisioned that the link 100 formed between mobile device 10 and the proximity beacon 20 is likely to be a wireless link.

The link 100 may be based on any of a variety (or combination) of communications technologies by which signals may be exchanged, including without limitation, wired technologies employing electrically and/or optically conductive cabling, and wireless technologies employing infrared, radio frequency or other forms of wireless transmission. It is envisioned that one or more of these links may be implemented as channels of communication (e.g., virtual private network (VPN) channels or other forms of virtual channels) formed between computing devices through portions of the Internet.

Generally, and in various embodiments, the link will use signaling and/or protocols conforming to any of a variety of industry standards, including without limitation, RS-232C, RS-422, USB, Ethernet (IEEE-802.3) or IEEE-1394. Alternatively or additionally, where one or more portions of the link 100 employs wireless signal transmission, one or more of the interfaces 17 and 47 may employ signaling and/or protocols conforming to any of a variety of industry standards, including without limitation, IEEE 802.11a, 802.11b, 802.11g, 802.16, 802.20 (commonly referred to as "Mobile Broadband Wireless Access"); Bluetooth; ZigBee; or a cellular radiotelephone service such as GSM with General Packet Radio Service (GSM/GPRS), CDMA/1xRTT, Enhanced Data Rates for Global Evolution (EDGE), Evolution Data Only/Optimized (EV-DO), Evolution For Data and Voice (EV-DV), High Speed Downlink Packet Access (HSDPA), High Speed Uplink Packet Access (HSUPA), 4G LTE, etc.

The mobile device 10 may store instructions to be executed by processor 15 in storage 11, such as control routine 18. The storage 11 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information As such, and in various embodiments, storage 11 may provide volatile and/or nonvolatile storage of data, data structures, computer-executable instructions, and so forth. For example, a number of program modules can be stored in memory units, including an operating system, and control routine 180.

The mobile device 10 may execute processing operations or logic using a processing circuit 15 in communication with control routine 18. The processing circuit 15 may comprise various hardware elements, software elements, or a combination of both. Examples of hardware elements may include devices, logic devices, components, processors, microprocessors, circuits, processor circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The processor circuit 15 may be caused by control routine 18 to initiate a registration process. During the registration process, the operator is prompted for various pieces of personal information concerning the operator such as a name, an address, contact information, account information, etc. The customer may also be prompted to choose whether to opt-in, and if so, to which kinds of messages.

The mobile device 10 may execute other communications operations using link interface 17 and communications and other routines contained in the control routine 18. The link interface 17 may implement any well-known communications techniques and protocols, such as techniques suitable for use with packet-switched networks (e.g., public networks such as the Internet, private networks such as an enterprise intranet, and so forth), circuit-switched networks (e.g., the public switched telephone network), or a combination of packet-switched networks and circuit-switched networks (with suitable gateways and translators). The link interface 17 may include various types of standard communication elements, such as one or more communications interfaces, network interfaces, network interface cards (NIC), radios, wireless transmitters/receivers (transceivers), wired and/or wireless communication media, physical connectors, and so forth. By way of example, and not limitation, link interface 17 may enable communication including wired communications media and wireless communications media. Examples of wired communications media may include a wire, cable, metal leads, printed circuit boards (PCB), backplanes, switch fabrics, semiconductor material, twisted-pair wire, co-axial cable, fiber optics, a propagated signal, USB and so forth. Examples of wireless communications media may include acoustic, radio-frequency (RF) spectrum, infrared and other wireless media.

In various embodiments, and as will be explained in greater detail, a user of the mobile device 10 uses the mobile device 10 to engage in online activities involving interactions between the mobile device 10 and one or more servers through a network. Examples of such interactions may entail browsing a website, requesting the performance of a financial or other transaction, sending and/or receiving email, and searching for information.

In executing a sequence of instructions of at least the control routine 14, the processor circuit 15 is caused to employ the controls 14 and the display 12 in providing an operator interface to the operator of the mobile device 10 that enables the operator to operate the mobile device 10 to engage in online interactions with other computing devices (e.g., the proximity beacon 20 or server 40) through the mobile device 10.

The controls 12 may comprise a pointing device, such as a mouse, touchpad or touchscreen, enabling selection of visually presented objects, or a keyboard or keypad. In various embodiments, the controls 12 may comprise any of a variety of types of manually-operable controls, including without limitation, lever, rocker, pushbutton or other types of switches; rotary, sliding or other types of variable controls; touch sensors, proximity sensors, heat sensors or bioelectric sensors, etc. The controls 12 may comprise manually-operable controls disposed upon a casing of corresponding ones of the mobile computing device 10, and/or may comprise manually-operable controls disposed on a separate casing of a physically separate component of corresponding ones of these computing devices (e.g., a remote control coupled to other components via infrared signaling). Alternatively or additionally, the controls 12 may comprise any of a variety of non-tactile operator input components, including without limitation, a microphone by which sounds may be detected to enable recognition of a verbal command; a camera through which a face or facial expression may be recognized; an accelerometer by which direction, speed, force, acceleration and/or other characteristics of movement may be detected to enable recognition of a gestures.

In various embodiments, the server 40 is a computing device with typical components as described above and a control routine 48. The control routine 48 includes instructions to be executed by a processor 45 to cause the server 40 to interact with a mobile device 10, also described above FIG. 2 illustrates a block diagram of a portion of the block diagram of FIG. 1 in greater detail. More specifically, aspects of the operating environments of the mobile device 10 and the server 40, in which their respective processor circuits 15 and 45 (shown in FIG. 1) are caused by execution of their respective control routines 18 and 48 to perform the aforedescribed functions are depicted. As will be recognized by those skilled in the art, each of the control routines 18 and 48, including the components of which each is composed, are selected to be operative on whatever type of processor or processors that are selected to implement each of the processor circuits 15 and 45.

In various embodiments, one or more of the control routines 18 and 48 may comprise a combination of an operating system, device drivers and/or application-level routines (e.g., so-called "software suites" provided on disc media, "applets" obtained from a remote server, etc.). Where an operating system is included, the operating system may be any of a variety of available operating systems appropriate for whatever corresponding ones of the processor circuits 15 and 45, including without limitation, Windows™, OS X™, Linux®, or Android OS™. Where one or more device drivers are included, those device drivers may provide support for any of a variety of other components, whether hardware or software components, that comprise one or more of the computing devices 10 and 40.

The control routine 18 comprises a client component 18A executable by the processing circuit 15 to use the mobile device 10 to engage in online activity with other computing devices via one or more links of a network and/or the Internet. The client component 18A cooperates with the controls 12 and the display 18 (and/or possibly other input/output devices such as a microphone or speakers) to provide an operator interface for operation of the mobile device 10 by its operator. The client component 18A may be one or more of a web browser, a data file viewer, a text editor, a terminal emulator, an instant messaging client, an email communications client, etc. Thus, the client component 18A provides a remote operator interface for online activity conducted with another computing device, such as the server 40.

Generally, control routine 18 also includes a registration component 18B. The registration component 18B, when executed by the processor 45, causes the mobile device to conduct a registration process with the server 40. In one aspect of the invention, upon installation, the registration component 48B may request that the user provide information, such as name, address, and contact information, to the server 40 to create an account for the mobile device 10 and to associate the new account with any other accounts the user may have.

Each of the control routines 18 and 48 comprises a communications component 18C and 48C, respectively, executable by corresponding ones of the processing circuits 15 and 45 to operate corresponding ones of the interfaces 17 and 47 to transmit and receive signals variously via the link 100 as has been described. As will be recognized by those skilled in the art, each of the communications components 18C and 48C are selected to be operable with whatever type of interface technology is selected to implement each of the interfaces 17 and 47.

In some embodiments, the communications component 18C causes the processor circuit 15 to operate the interface 17 to seek proximity beacons within a relatively close vicinity to the mobile device 10 through use of a relatively short range wireless technology such that when a device such as proximity beacon 20 is detected, an assumption is made that the proximity beacon be relatively near to the mobile device 10.

Correspondingly, in such embodiments, the communications component 48C causes the processor circuit 45 to operate the interface 47 to be available to communications from mobile devices that are within a relatively close vicinity to a proximity beacon. With the detection by the mobile device 10 of the proximity beacon 20, the processors 15 and 45 are caused by the communications components 18C and 48C to operate the interfaces 17 and 57, respectively, to form the link 100 (shown in FIG. 1) therebetween. With the link 100 formed, the processor 15 is caused to operate the interface 17 to transmit identification data to the interface 47. The processor can use the data to cause the server 400 to retrieve customer information and then send it back via interface 47 to the mobile device 10 via the interface 17.

As discussed above, a user chooses whether to opt-in to receiving in-store notifications. If the customer has opted in, and having identified a local pharmacy, the user travels to that pharmacy, bringing the mobile device 10. Upon arriving at the store, the user comes into relatively close vicinity to the proximity beacon 20, thereby enabling the mobile device 10 and the server 40 to communicate via their respective interfaces 17 and 47. Following formation of the link 100, the mobile device 10 transmits identification information to the server 400. The processor circuit 45 is caused by the server component 48B to acquire relevant customer information for transmission back to mobile device 10.

Figure 3:
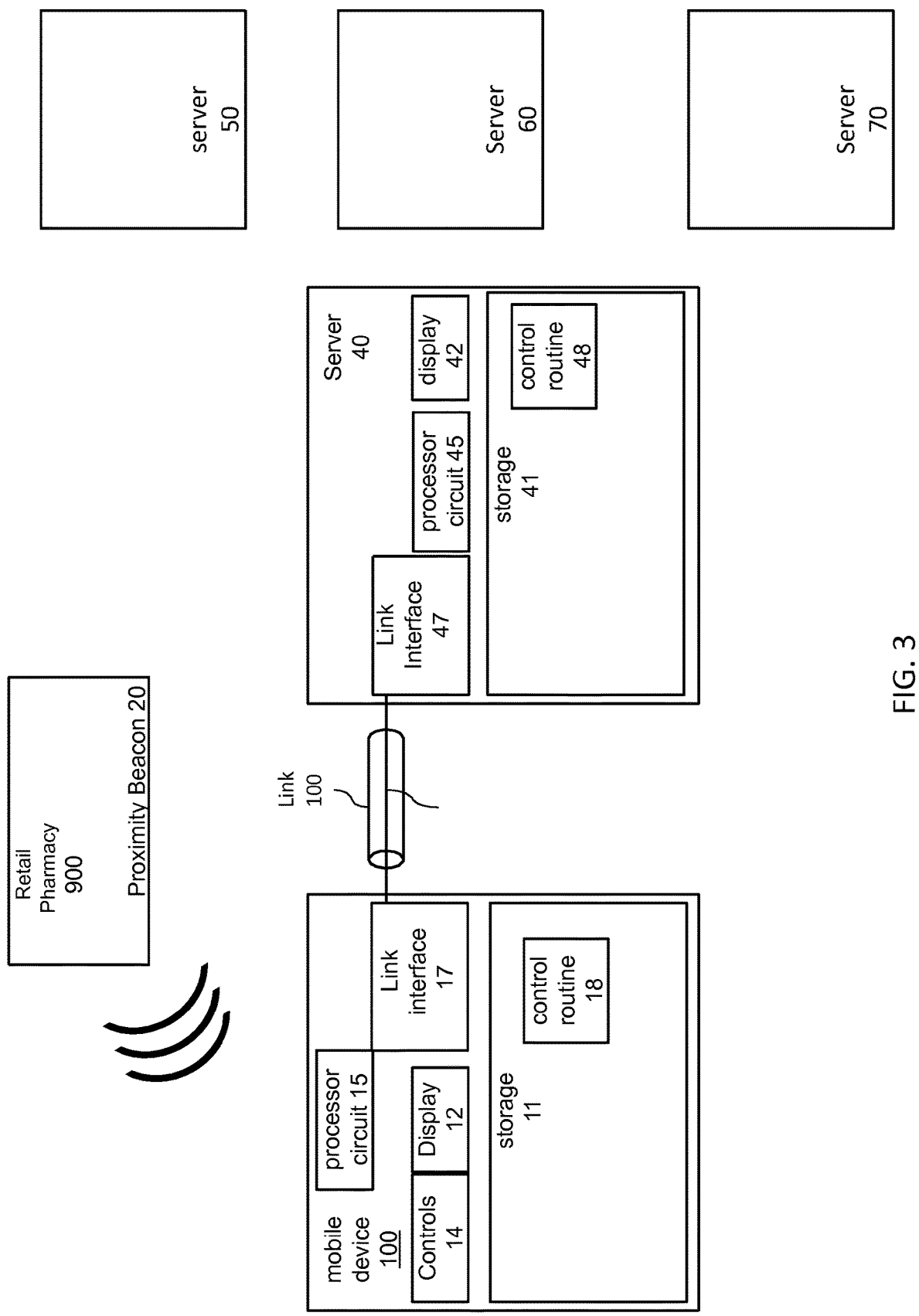
FIG. 3 is a block diagram of an embodiment of an in-store prescription notification system 1000.

FIG. 3 shows another embodiment of an in-store prescription notification system where the server 40 communicates with three (3) other servers 50, 60, and 70 to search for relevant customer information. These servers may contain information relating to other products and services of the retail pharmacy 900. For example, the retail pharmacy may provide photo development services, and the status of an order might be found on one of the servers 50, 60, or 70. The invention is not limited in terms of the number of servers or other sources of information that may be searched by server 40 for customer information. Other than the additional three (3) servers 50, 60, and 70, communicating with the server 40, the details of this embodiment may be substantially similar to the embodiment described above in connection with FIG. 1.

Figure 4:
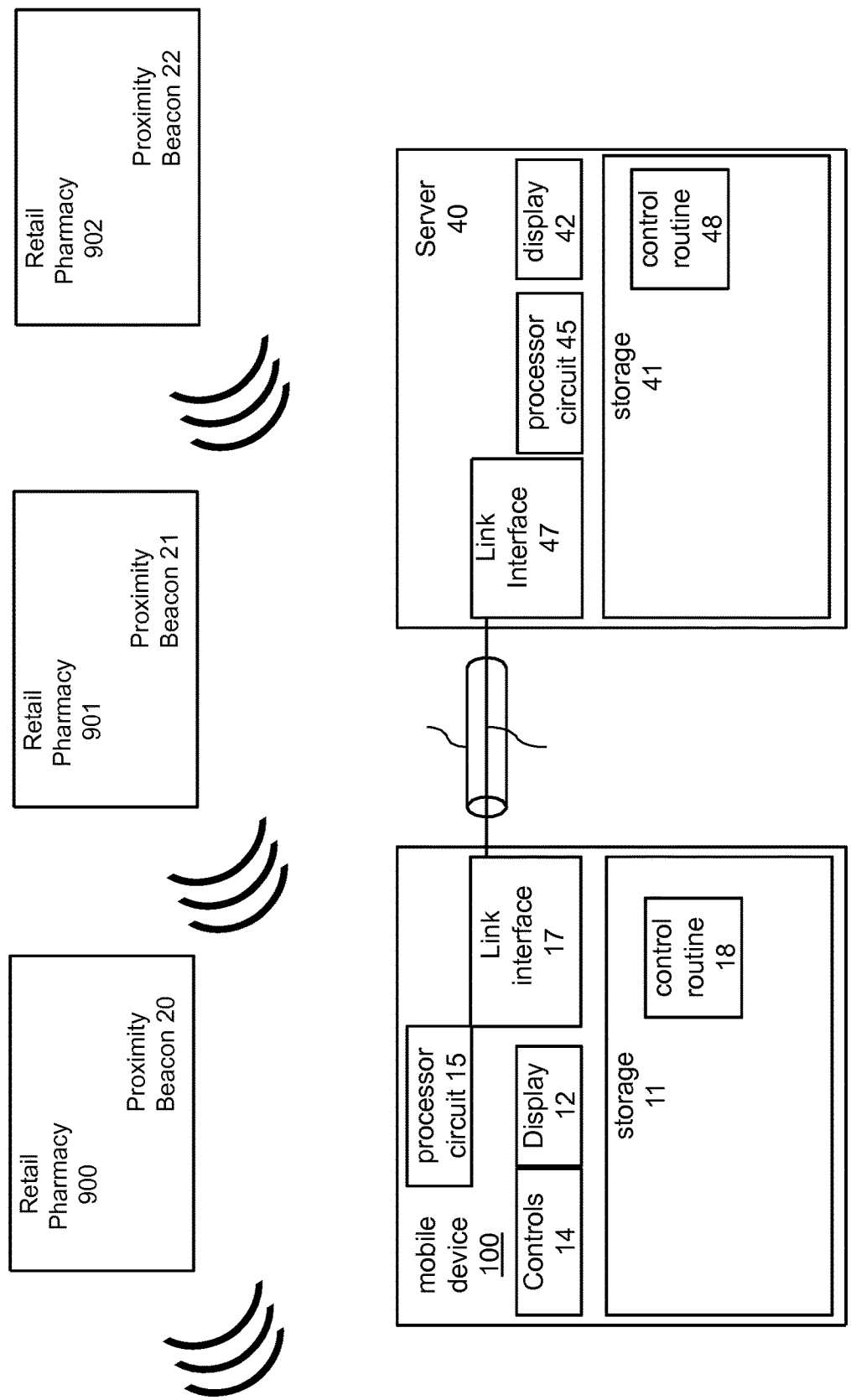
FIG. 4 is a block diagram of an embodiment of an in-store prescription notification system 1000.

FIG. 4 shows another embodiment of the in-store prescription notification system. In this and various other embodiments, there may be multiple physical locations, each of which has a proximity beacon. In FIG. 4, two additional physical locations are shown, retail pharmacy 901 and retail pharmacy 902, each with a respective proximity beam, 21 and 22. As with FIG. 3, the details of this embodiment may be substantially similar to the embodiment described above in connection with FIG. 1.

Figure 5:
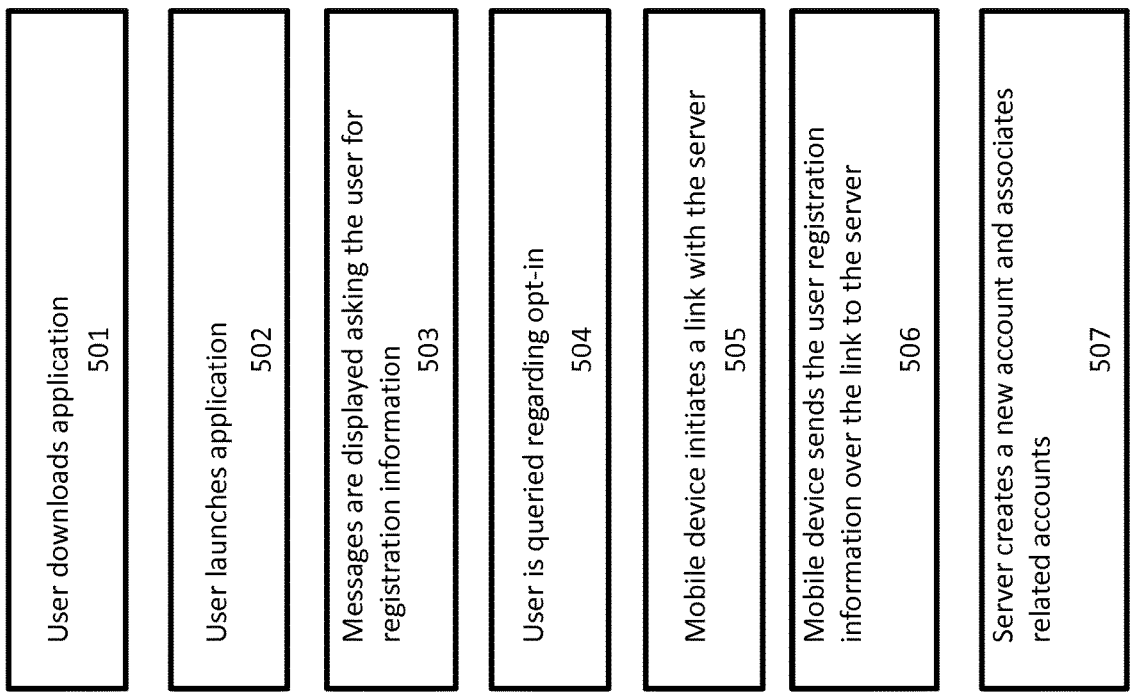
FIG. 5 is a flow of another embodiment of an in-store prescription notification system 1000.

FIG. 5 shows a first logic flow. The logic flow 500 may be representative of some or all of the operations executed by one or more embodiments described herein. More specifically, the logic flow 500 may illustrate operations performed by the processing circuit 15 of the mobile device 10 in executing at least the control routine 18 and the processing circuit 45 of the server 40 in executing at least the control routine 48. The flow 500 illustrates an embodiment of the registration process discussed above.

At 501, the user downloads or otherwise acquires a copy of an application which is included in control routine 48. At 502, the user launches the application for the first time. Recognizing the user is not yet registered, the user is requested to enter various identification information for registration at 503. In addition, at 504, the user is requested whether to opt-in to receive messages. In some embodiments, the user may also be requested to indicate which types of messages they wish to receive, for example, email, SMS, or other types of messages. The embodiments are not limited in this respect.

At 505, the mobile device initiates a link with the server, as described in detail above in connection with FIGS. 1 and 2. Once the link is established, the registration information is sent by the mobile device over the link to the server, at 506. The server can then create an account for the user, at 507, and associate any other related accounts that the user may have.

Figure 6:
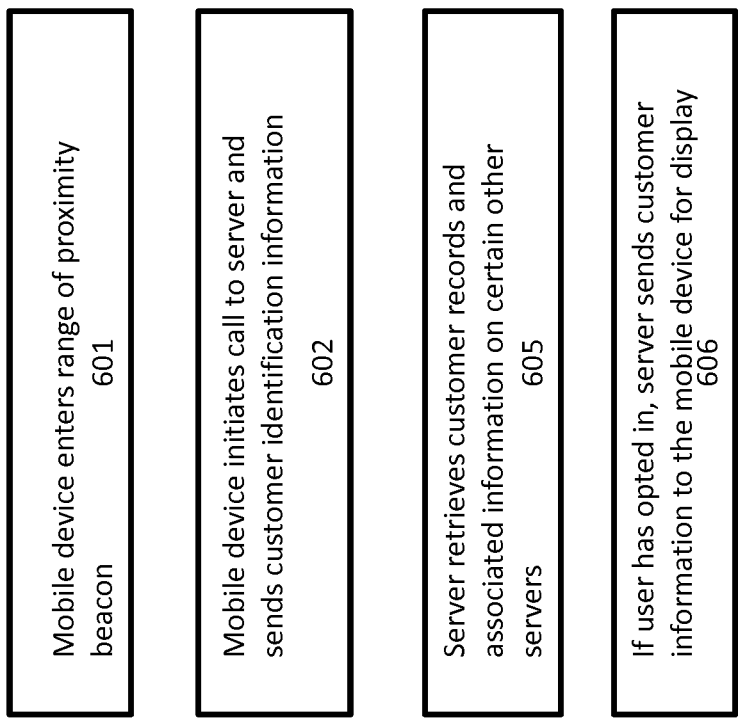
FIG. 6 is a flow of another embodiment of an in-store prescription notification system 1000.

FIG. 6 shows a second logic flow. As with the first logic flow 500, the second logic flow 600 may be representative of some or all of the operations executed by one or more embodiments described herein. Similarly, the logic flow 600 may illustrate operations performed by the processing circuit 15 of the mobile device 10 in executing at least the control routine 18 and the processing circuit 45 of the server 40 in executing at least the control routine 48.

At 601, the mobile device is brought into range of a proximity beacon by a user, for example, the user drives to that pharmacy and goes inside. In response to detecting the signal from the proximity beacon, the mobile device initiates a link with the server at 602. At 605-606, the server and mobile device exchange information. At 605, if the user opted-in during the registration process described above, the mobile device displays messages conveying the customer information.

FIG. 7 shows a third logic flow. As with the first logic flow 500, the third logic flow 700 may be representative of some or all of the operations executed by one or more embodiments described herein. Similarly, the logic flow 700 may illustrate operations performed by the processing circuit 15 of the mobile device 10 in executing at least the control routine 18 and the processing circuit 45 of the server 40 in executing at least the control routine 48.

At 701, it is assumed that the user is already at a pharmacy and the user's mobile device has established a link with a server. If the customer opted-in during the registration process and has prescriptions that are eligible for refill, the server sends that information to the mobile device. At 702, the mobile device displays a message to the user regarding the prescription that is eligible for refill, and asks whether the user would like to have the prescription refilled now. If the user indicates via the mobile device that they would like to refill the prescription, that information is sent to the server, and the server sends the information to the pharmacy so that it can be refilled. Then, at 704, when the prescription is ready for pickup, the mobile device receives that information, and displays a message to the user that the prescription is ready to pick-up.

Figure 8:
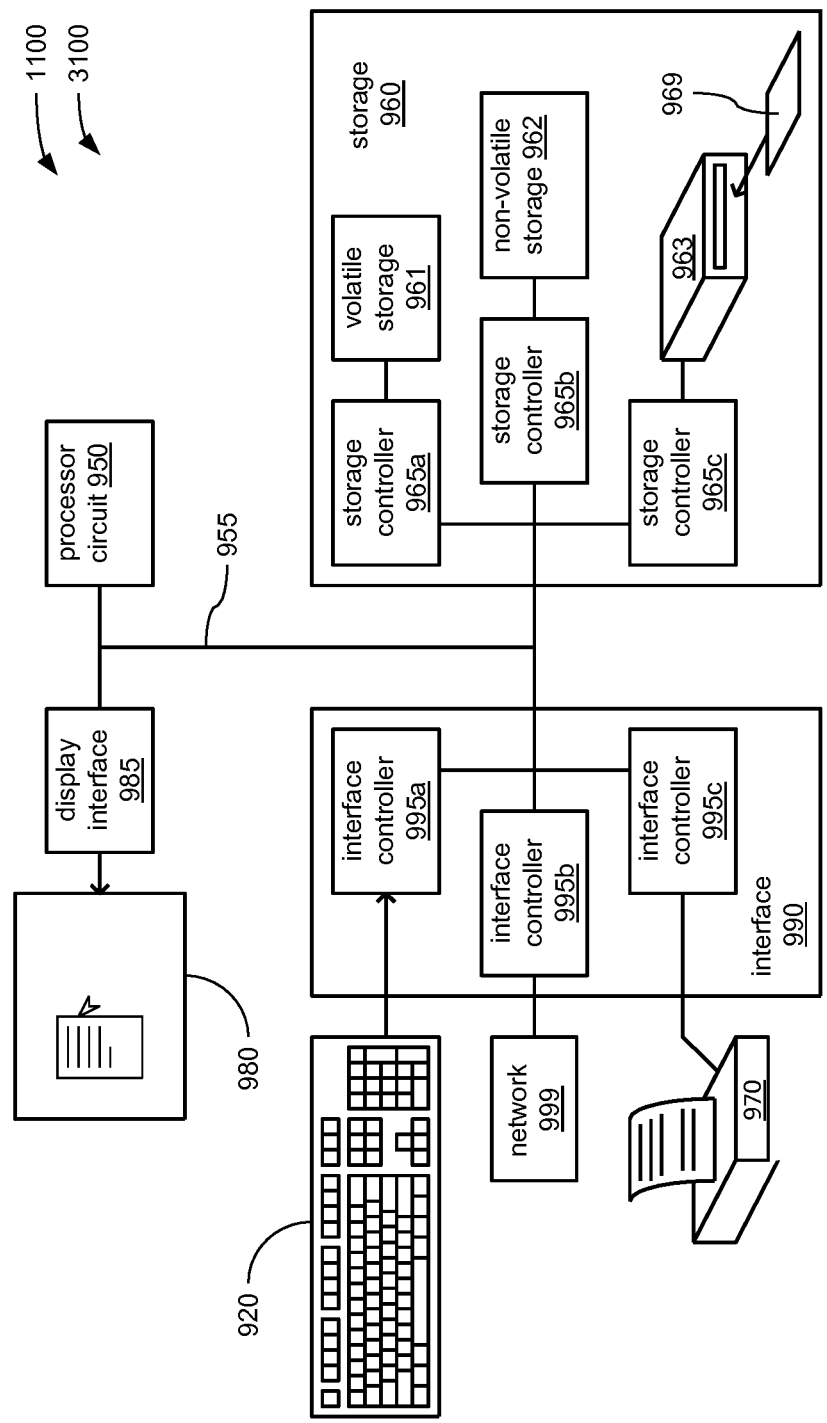
FIG. 8 is a block diagram of a computer architecture.

FIG. 8 shows an embodiment of an exemplary computing architecture 1100 suitable for implementing various embodiments as previously described. In one embodiment, the computing architecture 1100 may comprise or be implemented as part of an electronic device. Examples of an electronic device may include those described with reference to FIG. 1, among others. The embodiments are not limited in this context.

As used in this application, the terms "system" and "component" are intended to refer to a computer-related entity, either hardware, a combination of hardware and software, software, or software in execution, examples of which are provided by the exemplary computing architecture 1100. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1100 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1100.

As shown in FIG. 8, the computing architecture 1100 comprises a processing unit 1104, a system memory 1106 and a system bus 1108. The processing unit 1104 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1104.

The system bus 1108 provides an interface for system components including, but not limited to, the system memory 1106 to the processing unit 1104. The system bus 1108 can be any of several types of bus structure that may further interconnect to a memory bus (with or without a memory controller), a peripheral bus, and a local bus using any of a variety of commercially available bus architectures. Interface adapters may connect to the system bus 1108 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 1100 may comprise or implement various articles of manufacture. An article of manufacture may comprise a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

The system memory 1106 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 11, the system memory 1106 can include non-volatile memory 1110 and/or volatile memory 1112. A basic input/output system (BIOS) can be stored in the non-volatile memory 1110.

The computer 1102 may include various types of computer-readable storage media in the form of one or more lower speed memory units, including an internal (or external) hard disk drive (HDD) 1114, a magnetic floppy disk drive (FDD) 1116 to read from or write to a removable magnetic disk 1118, and an optical disk drive 1120 to read from or write to a removable optical disk 1122 (e.g., a CD-ROM or DVD). The HDD 1114, FDD 1116 and optical disk drive 1120 can be connected to the system bus 1108 by a HDD interface 1124, an FDD interface 1126 and an optical drive interface 1128, respectively. The HDD interface 1124 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, a number of program modules can be stored in the drives and memory units 1110, 1112, including an operating system 1130, one or more application programs 1132, other program modules 1134, and program data 1136. In one embodiment, the one or more application programs 1132, other program modules 1134, and program data 1136 can include, for example, the various applications and/or components of the system 100.

A user can enter commands and information into the computer 1102 through one or more wire/wireless input devices, for example, a keyboard 1138 and a pointing device, such as a mouse 1140. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1104 through an input device interface 1142 that is coupled to the system bus 1108, but can be connected by other interfaces such as a parallel port, IEEE 1394 serial port, a game port, a USB port, an IR interface, and so forth.

A monitor 1144 or other type of display device is also connected to the system bus 1108 via an interface, such as a video adaptor 1146. The monitor 1144 may be internal or external to the computer 1102. In addition to the monitor 1144, a computer typically includes other peripheral output devices, such as speakers, printers, and so forth.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

What is claimed is:

1. A method comprising:
    registering a user device of a customer;
    receiving a signal at the user device from a proximity beacon in a store;
    in response to receiving the signal from the proximity beacon, establishing a link between the user device in the store and a first server;
    providing user information from the user device of the customer to the first server via the link;
    receiving over the link with the user device in the store an in-store reminder from a database stored on the first server, the in-store reminder based on customer information identified by the user information, the in-store reminder notifying the user device of the customer identified by the customer information of a prescription that is eligible for a refill, wherein eligibility for the refill stored at the first server is sent to the user device in response to the user device receiving the signal at the store;
    causing the user device to display the in-store reminder of the eligible refill based on the customer information in the store and in response to establishing the link; and
    in response to a selection based on the in-store reminder at the user device to refill the prescription, the first server sending the customer information of the prescription to the store to refill the prescription.

2. The method of claim 1 wherein registering the user device comprises requesting a user to indicate whether to opt-in.

3. The method of claim 2 wherein the proximity beacon is a one-way transmitter device or a two-way transmitter and receiver device.

4. The method of claim 3 wherein the customer information comprises identification of at least one prescription that is eligible for refill.

5. The method of claim 3 wherein the customer information comprises identification of at least one prescription that is ready for pickup.

6. The method of claim 3 wherein the customer information comprises at least one coupon related to a user's profile.

7. The method of claim 3 wherein the first server requests customer information from a second server, which may or may not be identical to the first server.

8. The method of claim 3 wherein the user device receives the customer information only if the user opted in.

9. An apparatus comprising:
    a processor circuit;
    a link interface operative to communicatively couple the processor circuit to a network; and
    a storage communicatively coupled to the processor circuit and arranged to store a sequence of instructions operative on the processor circuit to:
    register a user device of a customer;
    receive a signal at the user device from a proximity beacon in a store;
    in response to receiving the signal from the proximity beacon, establish a link between the user device in the store and a server;
    provide user information from the user device of the customer to the server via the link;
    receive over the link with the user device in the store an in-store reminder from a database stored on the server, the in-store reminder based on customer information identified by the user information, the in-store reminder notifying the user device of the customer identified by the customer information of a prescription that is eligible for a refill, wherein eligibility for the refill stored at the server is sent to the user device in response to the user device receiving the signal at the store;

cause the user device to display the in-store reminder of the eligible refill based on the customer information in the store and in response to establishing the link; and send the customer information of the prescription to the store to refill the prescription in response to a selection based on the in-store reminder at the user device to refill the prescription.

10. The apparatus of claim 9, the instructions operative on the processor to cause a message to be displayed whether a user selects to opt-in.

11. The apparatus of claim 10, the proximity beacon comprising a one-way transmitter device.

12. The apparatus of claim 11, the user information comprising information about at least one prescription that is eligible for refill.

* * * * *